(12) United States Patent
　　Jain et al.

(10) Patent No.: US 12,653,958 B2
(45) Date of Patent: Jun. 16, 2026

(54) SEQUENTIAL DRUG DELIVERY SYRINGE

(71) Applicant: Becton, Dickinson and Company, Franklin Lakes, NJ (US)

(72) Inventors: Shashwat Jain, Indore (IN); Praveen Nalawade, Belgaum (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 791 days.

(21) Appl. No.: 17/990,874

(22) Filed: Nov. 21, 2022

(65) Prior Publication Data

US 2024/0165342 A1 May 23, 2024

(51) Int. Cl.
　　*A61M 5/315* (2006.01)
　　*A61M 5/28* (2006.01)

(52) U.S. Cl.
　　CPC ........ *A61M 5/31596* (2013.01); *A61M 5/284* (2013.01); *A61M 5/31511* (2013.01); *A61M 2005/31516* (2013.01); *A61M 2005/31598* (2013.01); *A61M 2207/10* (2013.01)

(58) Field of Classification Search
　　CPC .......... A61M 5/31596; A61M 5/31511; A61M 2005/31516; A61M 5/284
　　See application file for complete search history.

(56) References Cited

U.S. PATENT DOCUMENTS 4,171,698 A 10/1979 Genese
6,723,074 B1 4/2004 Halseth et al.

6,997,910 B2 2/2006 Howlett et al.
9,586,008 B2 3/2017 Shetty et al.
9,950,114 B2 4/2018 Thorne, Jr. et al.
2002/0035351 A1 3/2002 Lodice
2009/0287184 A1 11/2009 Lee
2015/0343153 A1 12/2015 Granelli

FOREIGN PATENT DOCUMENTS

GB 2229374 A 9/1990
WO 0211793 A1 2/2002

OTHER PUBLICATIONS

"PCT International Search Report and Written Opinion in PCT/US2023/080457 dated Feb. 27, 2024, 13 pages".

*Primary Examiner* — Bradley J Osinski

(74) *Attorney, Agent, or Firm* — Servilla Whitney LLC

(57) ABSTRACT

A dual chamber, sequential delivery syringe facilitates selective drug mixing, dosing, and administration through catheters or other vascular accessing devices (VADs), as well as post-administration flushing of catheters with a single syringe instrument. A syringe barrel incorporates an outlet, such as a Luer connector, a variable-volume, primary fluid chamber, and a secondary chamber that is pre-filled with fluid. A plunger manipulated, telescoping actuator, in conjunction with a medication stopper disposed within the barrel interior, form a valve for selectively isolating the secondary fluid chamber from fluid communication with the primary fluid chamber and/or the outlet of the syringe barrel. Valve opening is accomplished automatically by continuous advancement of the plunger.

20 Claims, 12 Drawing Sheets

SEQUENTIAL DRUG DELIVERY SYRINGE

TECHNICAL FIELD

The present disclosure generally relates to a dual chamber, sequential drug delivery syringe for administering two fluids, or for administering and flushing catheters and other vascular accessing devices (VADs), or for mixing and administering fluids, and methods for sequential drug delivery via a single syringe.

BACKGROUND

VADs are commonly used therapeutic devices and include I.V. catheters. There are two general classifications of VADs: peripheral catheters and central venous catheters. If not properly maintained, VADs can become occluded. To ensure VADs are used properly and do not become occluded, standards of practice have been developed. These standards include a cleaning procedure, which is commonly referred to as a flush procedure or flushing a catheter.

VAD standards of practice usually recommend flush procedures be performed after catheter placement, before fluid infusion, and before and after drug administration, blood sampling, transfusions, and parenteral nutrition. The goal of these flush procedures is to confirm catheter patency, avoid drug incompatibilities, ensure the complete drug dose administration, prevent thrombus formation, and minimize the risk of blood stream infections. Flush procedures require diverse types and amounts of flush solutions. Commonly used flush solutions are saline and/or heparin lock solution. The type of flush solution and amount vary depending on the specific type of catheter. Flush solution volumes between 5 and 10 ml are most common but can range from 1 ml to 20 ml.

For flush procedures, an I.V. line refers to a system containing a VAD, a tubing set with clamp and may terminate with a port or valve. The most common types of ports are covered by pierceable septums or pre-slit septums and are known in the art and sometimes referred to as "PRN" from the Latin pro re nata meaning "as the need arises". The septum is preferably made of rubber or another elastomeric material, which permits insertion of a sharp needle cannula to infuse fluids or to withdraw fluids from the catheter. Upon withdrawal of the needle cannula the septum seals itself. Ports having pre-slit septums are used with blunt cannula or the frusto-conically shaped tip of a syringe barrel. The syringe tip or the blunt cannula (which is usually attached to a syringe) is gently pushed through the pre-slit septum to establish fluid communication.

I.V. valves, another type of terminal I.V. access device that does not require a needle having a sharp tip, are activated by the frusto-conically shaped tip (e.g., a Luer connector) of a syringe barrel to allow fluid communication between the interior of the syringe and the catheter. These valves may contain structure for delivering fluid from a storage compartment in the valve to the catheter and are referred to in the art as positive displacement valves.

The removal of debris or residue is referred to as "purging" or "flushing" and prevents the build-up of deposits of blood, blood residue and IV drugs within a catheter or other VAD device. Such build-up can cause partial or complete blockage of the fluid pathway in a catheter system and can also require expensive and potentially dangerous methods for purging the affected catheter or a total catheter exchange. Often, such blockages lead to interruptions in therapy that may compromise patient care. The build-up of residue within a catheter can also increase infection risk by providing a breeding medium for microorganisms.

As is understood by one skilled in the art, flushing techniques involve injecting a flush solution, e.g., a saline solution, into VADs to clear debris and blockage. Injection is commonly done by a advancing a plunger rod into a pre-filled syringe barrel thereby expelling the flush solution into the VAD. When such techniques are used in conjunction with catheters, turbulence is introduced within the catheter, moving any debris or residue attached to the catheter. Flushing techniques require the application of substantially constant pressure or force to the plunger rod in the distal direction. Conventional or smooth flushing techniques may also include the application of pressure or force that increases or decreases substantially linearly to the plunger rod in the distal direction.

After flushing, the practitioner is then able to administer a dosage of medical fluid, the fluid being in a vial which requires withdrawal therefrom, or in a separate pre-filled syringe. However, the connecting of multiple devices to a VAD introduces the connectors to an unsterile outside environment, thereby introducing the possibility of transmitting a catheter related bloodstream infection (CRBSI), which can be costly and potentially lethal. To decrease CRBSI cases and to ensure VAD's are used and maintained correctly, standards of practice have been developed, which include disinfecting and cleaning procedures.

Administration of intravenous medication followed by IV flush, typically utilizes two separate syringes in clinical practice. Flushing is performed after medication administration, as residual medicine may remain in the luer portion of the drug delivery syringe and in the catheter. Without a subsequent flushing procedure, the full medication dosage may not be delivered to the patient. Some medications are administration time sensitive and should not remain in the catheter until a subsequent medicine administration flushes the residual quantity of the prior medication through the line. Sequential flushing with a second syringe is performed to resolve the residual medication delivery issue, but use of a second, flushing syringe has certain disadvantages, namely: potential delivery medication error and failure to follow up medication delivery with flushing procedure. Potential medication delivery is possible, as most commonly utilized are colorless, as are the saline and other flushing solutions. Failure to deliver the flushing solution after medication delivery may occur if the administering healthcare professional becomes distracted during the procedure.

There is a need for a syringe assembly which has the means to both flush a VAD and administer a dosage of medical fluid, thereby reducing the risk of CRBSI. There is also a need for a single syringe for administration of intravenous medication followed by IV flush, to increase clinician efficiency, and reduce costs associated with maintaining syringe inventory, and medical waste disposal. There is an additional need for a single syringe, for mixing medication in powdered form and thereafter administering the mixed medication to a patient.

SUMMARY

A dual chamber, sequential drug delivery syringe facilitates selective drug mixing, dosing, and administration through catheters or other vascular accessing devices (VADs), as well as post-administration flushing of catheters with a single syringe instrument. Syringes disclosed herein are utilized as a sequential syringe in which the saline or other flushing fluid is prefilled in one chamber and the other chamber is prefilled with medication or filled on-site by a healthcare professional. In other embodiments, the sequential drug delivery syringe is utilized as a drug mixing syringe, prefilled with saline or another diluent in one chamber, with powdered/lyophilized drug in the other chamber. A syringe barrel incorporates an outlet, such as a Luer connector, primary and secondary fluid chambers. A telescoping actuator assembly, coupled to a plunger stopper, functions as an isolation valve for selectively opening or blocking a through-passage formed in a medication stopper. The telescoping actuator assembly selectively isolates the secondary chamber from the primary chamber, solely by advancement of a syringe plunger. Use of syringes of the type disclosed herein, in medical procedures requiring both flushing and administration of drugs through catheters or other VADs, reduces the need to perform multiple infusions and withdrawals of multiple, single-function syringes. Use of the disclosed syringes advantageously reduces risk of patient infection, reduces costs associated with syringe inventory and subsequent waste disposal, and reduces clinician time necessary to complete the associated medical procedures.

One aspect of the present disclosure pertains to a sequential delivery syringe, which includes a hollow syringe barrel defining an inner wall, a proximal barrel end and a distal barrel end. The distal end of the barrel includes a connector defining an outlet lumen therethrough. The outlet lumen is in fluid communication with an interior of the barrel. The barrel interior is defined by barrel's the open proximal end, the distal end, and the inner side wall. The syringe includes a plunger disposed with the barrel interior, having a proximal end extending outside of the proximal end of the barrel and a distal end. The syringe includes a secondary or saline stopper disposed within the barrel interior, having a proximal axial end coupled to the distal end of the plunger, and a distal axial end defining a distal cavity. A primary stopper or medication stopper is disposed within the barrel interior between the secondary stopper and the distal end of the barrel. The primary or medication stopper has a proximal axial end defining a proximal cavity, a distal axial end defining a distal cavity with a seating surface, and a through-passage in fluid communication with both of its proximal and distal cavities. A telescoping actuator assembly is oriented with the respective cavities of the primary and secondary stoppers. The actuator assembly functions as a valve to isolate the proximal cavity of the primary stopper from its distal cavity. The actuator assembly comprises a reciprocating actuator oriented within the through-passage of the primary stopper. The actuator projects into the proximal and distal cavities of the primary/medication stopper and has an outer circumferential surface that is in sliding, friction engagement with the through-passage, and a radially projecting, proximal axial face that is oriented within the corresponding distal cavity of the primary stopper, in opposed orientation with the seating surface. The actuator assembly also comprises a tube having: an outer circumferential surface coupled to and within the distal cavity of the secondary stopper, and an inner wall circumscribing and in sliding, friction engagement with the outer circumferential surface of the actuator. The syringe has a primary fluid chamber within the barrel interior, is defined between the distal end surface of the primary stopper and outlet lumen at the distal end of the barrel. Volume of the primary fluid chamber is selectively variable by translation of the plunger. The syringe has a secondary fluid chamber, within the barrel interior, defined between the distal end surface of the secondary stopper and the through-passage of the primary stopper. Volume of the secondary fluid chamber is selectively variable by translation of the plunger when the proximal axial face of the actuator is spaced away from the seating surface of the primary stopper. In this syringe embodiment, the secondary fluid chamber is in fluid communication with the primary fluid chamber and the outlet lumen of the syringe when the proximal axial face of the actuator is spaced away from the seating surface of the primary stopper, and the secondary fluid chamber is isolated from the primary fluid chamber when the proximal axial face of the actuator is in abutting contact with the seating surface of the primary stopper. When the syringe is used, withdrawal of the plunger tensions the telescoping actuator assembly, which reciprocates the proximal axial face of the actuator into abutting contact with the seating surface of the primary stopper and withdraws medication/primary stopper. When the syringe is used, advancement of the plunger alone advances the primary or medication stopper, reciprocates the proximal axial face of the actuator away from abutting contact with the seating surface of the primary stopper, advances the secondary or saline stopper, and collapses the telescoping actuator assembly within the respective distal cavity of the secondary stopper and the proximal cavity of the primary stopper.

In some embodiments of the syringe disclosed herein, its secondary chamber is pre-filled with flushing solution. Desirably, a clinician can administer a medication into a patient's VAD with the primary chamber and immediately flush the VAD with the second chamber, without removing the syringe from the VAD. In embodiments of the syringe disclosed herein, a clinician can administer medication through, and thereafter immediately flush, a VAD with a single, continuous advancement of a single plunger.

Another aspect of the present disclosure pertains to sequential drug delivery syringe. The syringe includes a hollow syringe barrel defining an inner wall, a proximal barrel end and a distal barrel end. The distal end of the barrel includes a connector defining an outlet lumen therethrough, with the outlet lumen in fluid communication with an interior of the barrel. The barrel's interior is defined by the open proximal end, the distal end, and the inner side wall. A plunger is disposed with the barrel interior, having a proximal end extending outside of the proximal end of the barrel and a distal end. A secondary or saline stopper is disposed within the barrel interior, having a proximal axial end coupled to the distal end of the plunger, and a distal axial end defining a distal cavity therein. A primary or medication stopper is disposed within the barrel interior between the secondary stopper and the distal end of the barrel. The primary stopper has a proximal axial end defining a proximal cavity, a distal axial end defining a distal cavity with a seating surface, and a through-passage in fluid communication with both of the proximal and distal cavities. The syringe also has a telescoping actuator assembly oriented with the respective cavities of the primary and secondary stoppers. The telescoping actuator assembly includes plural nested tubes in sliding, friction engagement with each other; each nested tube respectively has an outer circumferential surface and an inner wall. An outer circumferential surface of a most proximally oriented one of the nested tubes is coupled to and within the distal cavity of the secondary stopper, with its inner wall in sliding, friction engagement with the outer circumferential surface of an adjoining tube captured therein. A reciprocating actuator is oriented within the through-passage of the primary stopper. The actuator includes a collet bushing having an annular bushing rim, a radially projecting, proximal axial face thereof is in opposed orientation with a mating, annular-shaped seating surface of the primary stopper. The collet bushing has a plurality of collet bushing fingers projecting away from the proximal axial face of the annular bushing rim, in friction contact with the surface defining the through-passage. A distal tip of each bushing finger projects into the proximal cavity of the primary stopper. The distal tips of the collet bushing fingers are coupled to a platform oriented on a distal end of an actuator shaft. An outer surface of a proximal end of the actuator shaft is in sliding friction engagement with the inner wall of the distal-most oriented tube. The seating surface of the primary stopper is captured between the collet bushing and the platform. The syringe defines primary fluid chamber within the barrel interior, between the distal end surface of the primary stopper and outlet lumen at the distal end of the barrel. Volume of the primary fluid chamber is selectively variable by translation of the plunger. The syringe defines a secondary fluid chamber, within the barrel interior, between the distal end surface of the secondary stopper and the through-passage of the primary stopper. Volume of the secondary fluid chamber is selectively variable by translation of the plunger when the proximal axial face of the collet bushing's annular bushing rim is spaced away from the seating surface of the primary stopper. In this syringe, the secondary fluid chamber is in fluid communication with the primary fluid chamber and the outlet lumen of the syringe when the proximal axial face of the collet bushing's annular bushing rim is spaced away from the seating surface of the primary stopper, and the secondary fluid chamber is isolated from the primary fluid chamber when the proximal axial face of the annular bushing rim is in abutting contact with the seating surface of the primary stopper. When the syringe is used, withdrawal of the plunger tensions the telescoping actuator assembly, which reciprocates the proximal axial face of the collet bushing into abutting contact with the seating surface of the primary stopper and withdraws said stopper. When the syringe is in use, advancement of the plunger alone advances the primary stopper, reciprocates the proximal axial face of the actuator's collet bushing away from abutting contact with the seating surface of the primary stopper, advances the secondary stopper, and collapses the telescoping actuator assembly within the respective distal cavity of the secondary stopper and the proximal cavity of the primary stopper.

In some syringe embodiments of this disclosure, an inwardly radially projecting barrel ring is formed on the inner wall of the barrel, and a path seal inhibits backflow of fluid from the primary chamber to the secondary chamber. The path seal has an inner circumferential surface that circumscribes the outer surface of the tube of the actuator assembly, and an outer circumferential surface is in fluid sealing contact with the proximal cavity of the primary stopper.

Other aspects of the present disclosure pertain to a method for making the sequential delivery syringe disclosed herein by inserting the collet bushing fingers into the through-passage of the primary stopper so that they project into the proximal cavity. After the collet bushing insertion, the platform of the actuator assembly is coupled to the tips of the collet bushing fingers, capturing the primary stopper between the annular rim of the collet bushing and the cruciform platform. Next, the proximal-most oriented tube of the actuator assembly is coupled within the distal cavity of the secondary stopper, before or after coupling the plunger to the secondary stopper. The now coupled primary stopper, actuator assembly, secondary stopper and the plunger are inserted into the interior of the syringe barrel.

The respective features of the aspects and exemplary embodiments of the disclosure that are described herein may be applied jointly or severally in any combination or sub-combination.

BRIEF DESCRIPTION OF THE DRAWINGS

Exemplary embodiments of the disclosure are further described in the following detailed description in conjunction with the accompanying drawings, in which.

To facilitate understanding, identical reference numerals have been used, where possible, to designate identical elements that are common to the figures. The figures are not drawn to scale.

DETAILED DESCRIPTION

Figures 1, 2:
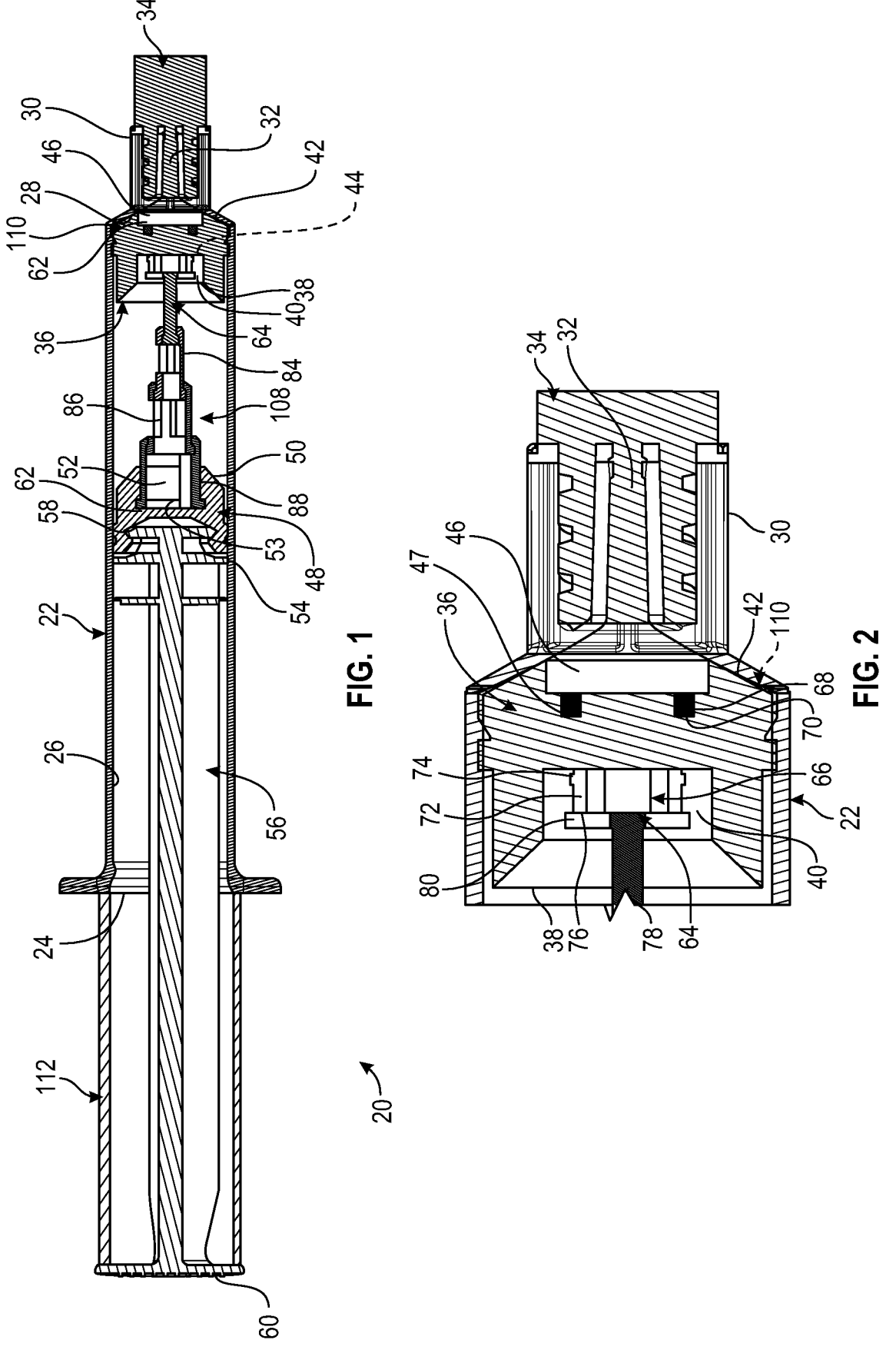
FIG. 1 is a cross-sectional view of an embodiment of a dual chamber syringe, where the secondary chamber is pre-filled with fluid and the primary, drug delivery chamber is collapsed.
FIG. 2 is an enlarged, cross-sectional view of the distal portion of the syringe of FIG. 1.

Aspects of the dual chamber syringe embodiments disclosed herein facilitate selective drug mixing, dosing, and administration through catheters or other vascular accessing devices (VADs), as well as post-administration flushing of catheters with a single syringe instrument. Generally, in each disclosed embodiment, a syringe barrel incorporates an outlet, such as a Luer connector, a variable-volume, primary fluid chamber, and a secondary chamber that is pre-filled with fluid, such as a saline flushing fluid. A plunger manipulated, telescoping actuator assembly, coupled to a secondary or saline plunger stopper, in conjunction with a primary or medication stopper disposed within the barrel interior, functions as an isolation valve for selectively blocking or opening a through-passage formed in a medication stopper. The telescoping actuator assembly selectively isolates the secondary fluid chamber from fluid communication with the primary fluid chamber and/or the outlet of the syringe barrel, solely by retraction of the syringe plunger. The telescoping actuator assembly selectively opens the through-passage solely by advancement of the syringe plunger.

The isolated, secondary chamber construction advantageously facilitates use of pre-packaged drugs or flushing solutions in that chamber, whereby a clinician can aspirate and dispense medication with the empty primary chamber and thereafter immediately deliver pre-packaged flushing solution from the secondary chamber. In other embodiments, the syringe disclosed herein is used as a drug mixing syringe, prepackaged with a powdered drug in the primary chamber and a diluent solution in the secondary chamber. In some embodiments, a single advancing stroke on the single plunger of the syringe automatically delivers or infuses, sequentially into the VAD, a drug contained in the primary chamber, followed by flushing solution.

In this disclosure, a convention is followed wherein the distal end of the device is the end closest to a patient, e.g., for delivery of one or more drugs to the patient, and the proximal end of the device is the end away from the patient and closest to a clinician or other medical practitioner. With respect to terms used in this disclosure, the following definitions are provided.

As used herein, the use of "a," "an," and "the" includes the singular and plural.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is associated with a flush syringe and can interlock and connect to the female end located on the vascular access device (VAD). A Luer connector also has a distal end channel that releasably attaches the Luer connector to the hub of a VAD, and a proximal end channel that releasably attaches the Luer connector to the barrel of a syringe.

As used herein, ISO 80369-7:2016 defines a specification for standard Luer connectors including a 6% taper between the distal end and the proximal end. A male standard Luer connector increases from the open distal end to the proximal end. A female standard Luer connector decreases from the open proximal end to the distal end. According to ISO 80369-7:2016, a male standard Luer connector has an outer cross-sectional diameter measured 0.75 mm from the distal end of the tip of between 3.970 mm and 4.072 mm. The length of the male standard Luer taper is between 7.500 mm to 10.500 mm. The outer cross-sectional diameter measured 7.500 mm from the distal end of the tip is between 4.376 mm and 4.476 mm. As used herein, the phrases "male standard Luer connector" and "female standard Luer connector" shall refer to connectors having the dimensions described in ISO 80369-7, which is hereby incorporated by reference in its entirety.

As would be readily appreciated by skilled artisans in the relevant art, while descriptive terms such as "tip", "hub", "thread", "protrusion/insert", "tab", "slope", "wall", "top", "side", "bottom" and others are used throughout this specification to facilitate understanding, it is not intended to limit any components that can be used in combinations or individually or to require specific spatial orientations, to implement various aspects of the embodiments of the present disclosure.

Before describing several exemplary embodiments of the disclosure, it is to be understood that the disclosure is not limited to the details of construction or process steps set forth in the following description. The disclosure is capable of other embodiments and of being practiced or being conducted in many ways.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

In an exemplary implementation of the embodiments of present disclosure, a barrel of a syringe includes a distal end having a needleless connection. In one or more embodiments, the needleless connection includes at least one thread and other features in all combinations allowing it to interface with a corresponding thread or plurality of threads of a corresponding connector.

According to further exemplary implementations of the embodiments of the present disclosure, configuration of structural elements making up the needleless connector include a collar protruding from the distal end of the barrel, the collar comprising at least one thread to connect to the corresponding thread or plurality of threads of a corresponding connector.

According to still further exemplary implementations of the embodiments of the present disclosure, the collar or the needleless connector may bend or elastically deform to allow better interference fit compliance with corresponding connectors.

According to still further exemplary implementations of the embodiments of the present disclosure, the needleless connector may comprise female threads that are sized and have a thread pattern that will engage with a standard ISO594-2 type of male fitting and/or male threads that are sized and have a thread pattern that will engage with a standard ISO594-2 type of female fitting. An example of an ISO594-2 type of fitting is a Q-style fitting.

In one or more embodiments, a female connector may be selected from the group consisting essentially of: needle-type connectors (for direct injection into a patient or insertion into a drug vial for aspiration of a drug dose therefrom), needle-free connectors, catheter Luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc.

In one or more embodiments, the male connector may be an intravenous tubing end or a stopcock.

Figure 3:
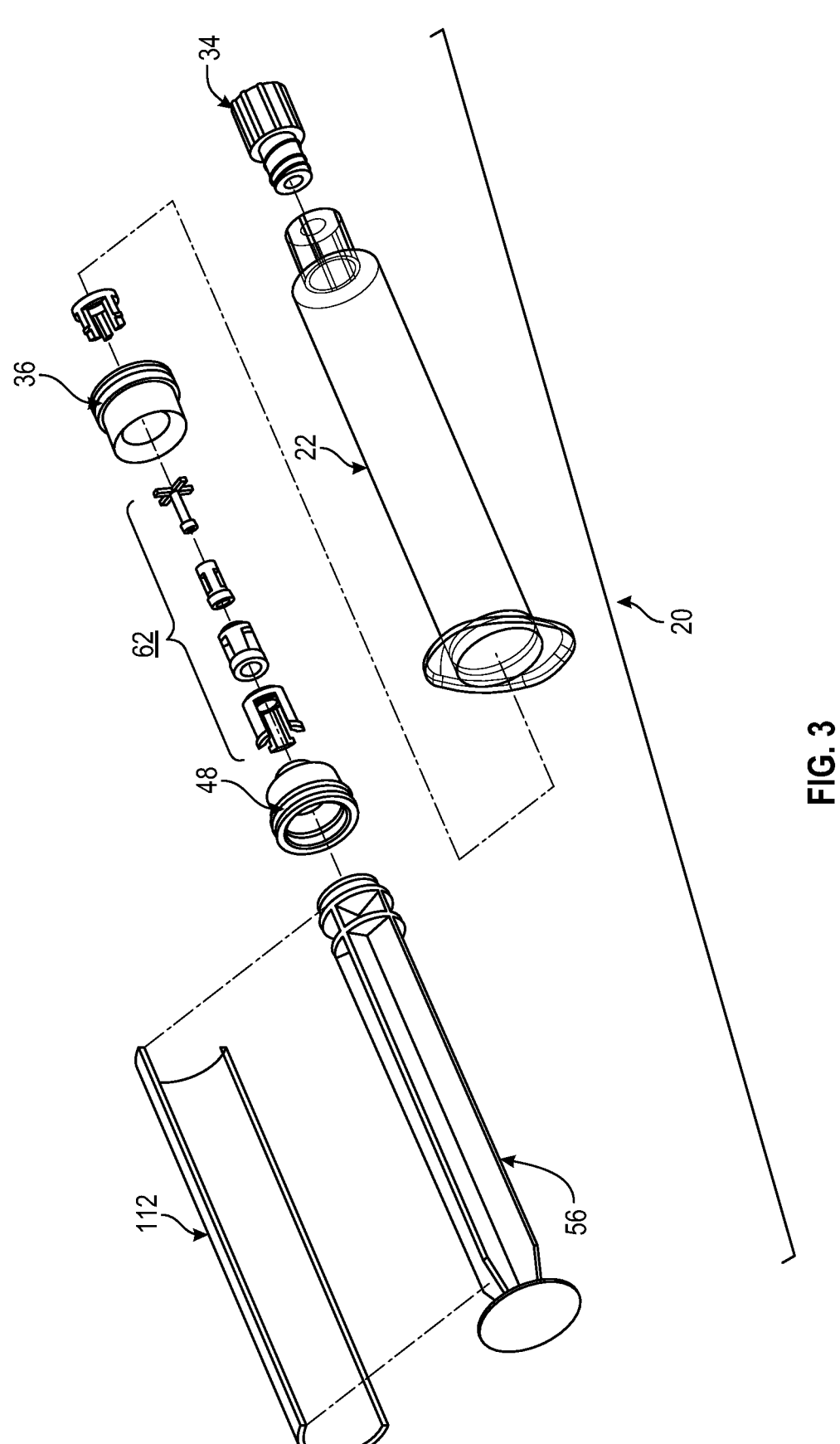
FIG. 3 is an exploded view of the syringe of FIG. 1.
Figure 4:
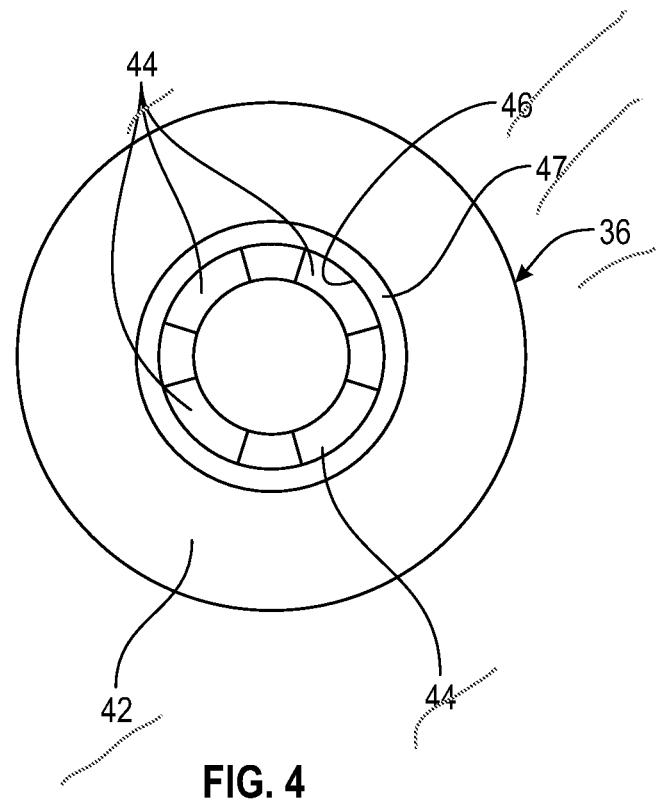
FIG. 4 is an axial end view of a medication stopper of the syringe of FIG. 1.

Referring now to the drawings, a first aspect of the present disclosure is shown in FIGS. 1-7. wherein a syringe 20 comprises a substantially cylindrically shaped barrel 22, which defines an open proximal end 24, an inner side wall 26, and a distal end 28. In other embodiments the barrel 22 comprises a non-cylindrical profile. The conical profile, distal end 28 of the barrel 22 includes a threaded Luer tip or connector 30 defining an outlet lumen 32, for attachment to and fluid communication with various associated VAD connectors (not shown). A threaded, selectively removeable male Luer cap 34 seals the outlet lumen from ambient air. Referring to FIGS. 1, 2 and 4, a primary or medication stopper 36, inserted within the syringe barrel 22, has a proximal axial end, which defines a proximal cavity 42, and a conical-profile distal axial end 42. Conical profile of the distal axial end 42 matches that of the distal end 28 of the syringe barrel 22, to facilitate complete emptying of fluids from the syringe. The proximal cavity 40 is in fluid communication with sector-shaped through-passages 44 and a distal cavity 46 defined within the medical stopper 36. An axially oriented seating surface 47 is defined within the distal cavity 46, circumscribing the sector-shaped through passages 44.

Referring to FIGS. 1 and 3, the syringe 20 incorporates a secondary or saline stopper 48, inserted within the barrel inner wall 26. The saline stopper 48 has a conical-profile distal end 50, which matches that of the proximate axial end 38 of the medication stopper 36. The saline stopper 48 defines a distal-end cavity 52 with a radial groove 53. A proximal end 54 of the saline stopper 48 is coupled to a distal end 58 of plunger 56. The proximal end 60 incorporates a finger manipulation pad.

Referring to FIGS. 1-7, a telescoping actuator assembly 60 couples the medication stopper 36, the saline stopper 48 and the plunger 56 under tension when the plunger is withdrawn. The actuator assembly 60 includes an actuator 64, with a collet bushing 66. The collet bushing 66 comprises an annular bushing rim 68, with a proximal face 70 thereof in opposed orientation with the annular seating surface 47 of the distal cavity 46 of the medication stopper 36. As shown specifically in FIG. 2, when the proximal face 70 of the annular rim 68 of the collet bushing 66 contacts and abuts the annular surface 47 of the medication stopper 36, it isolates the proximal cavity 40 of the medicine stopper 36, and any fluid contained therein, from the outlet 32 of the syringe 20, because fluid cannot flow through the through-passage 44 into the distal cavity 46.

Figure 5:
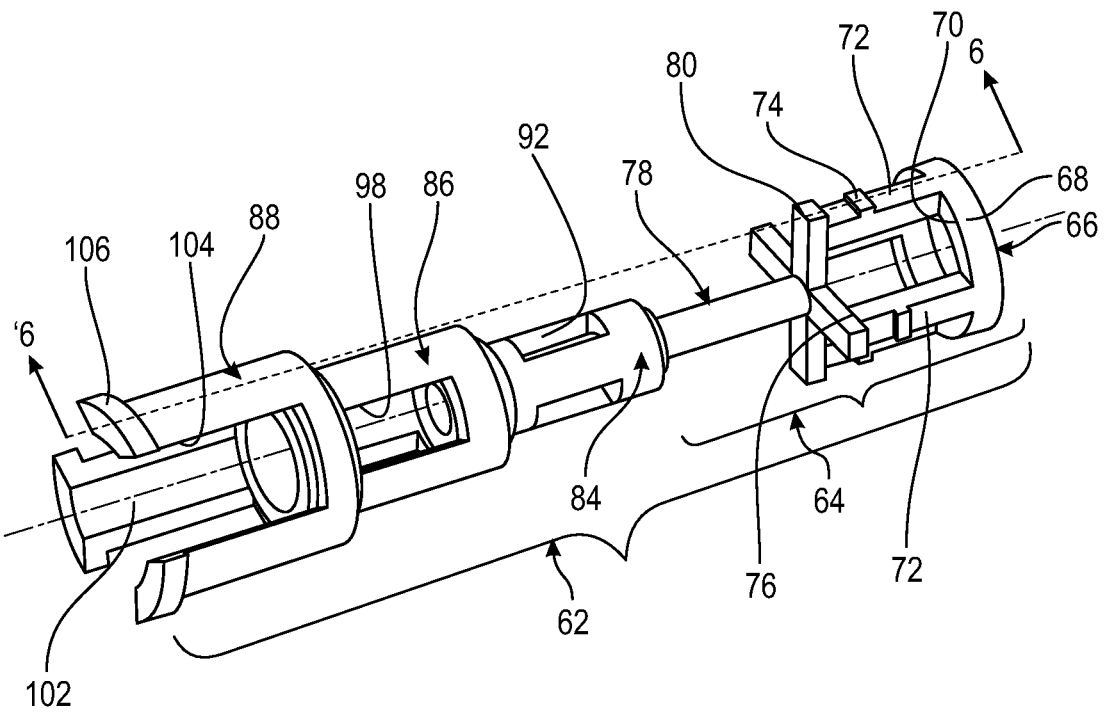
FIG. 5 is a perspective view of a telescoping actuator assembly of the syringe of FIG. 1 in its fully extended configuration.
Figure 6:
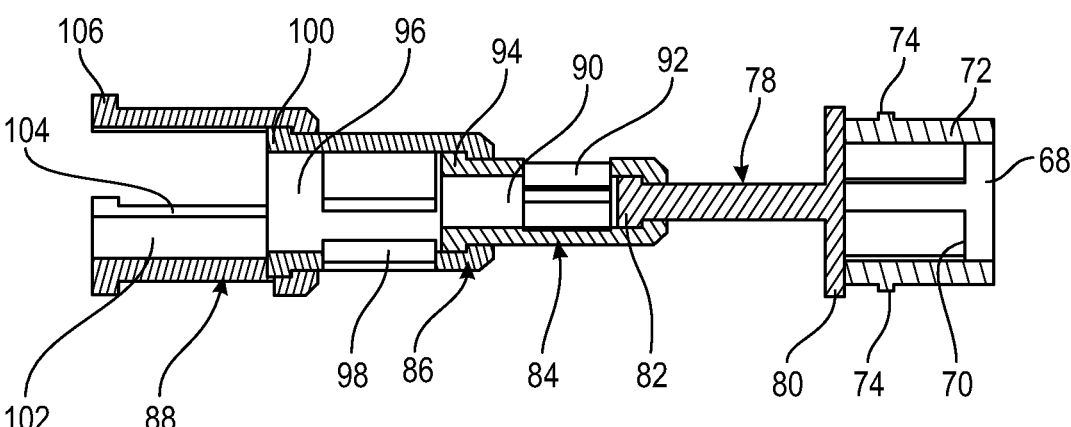
FIG. 6 is a cross-sectional view of the telescoping actuator assembly of FIG. 5.
Figure 7:
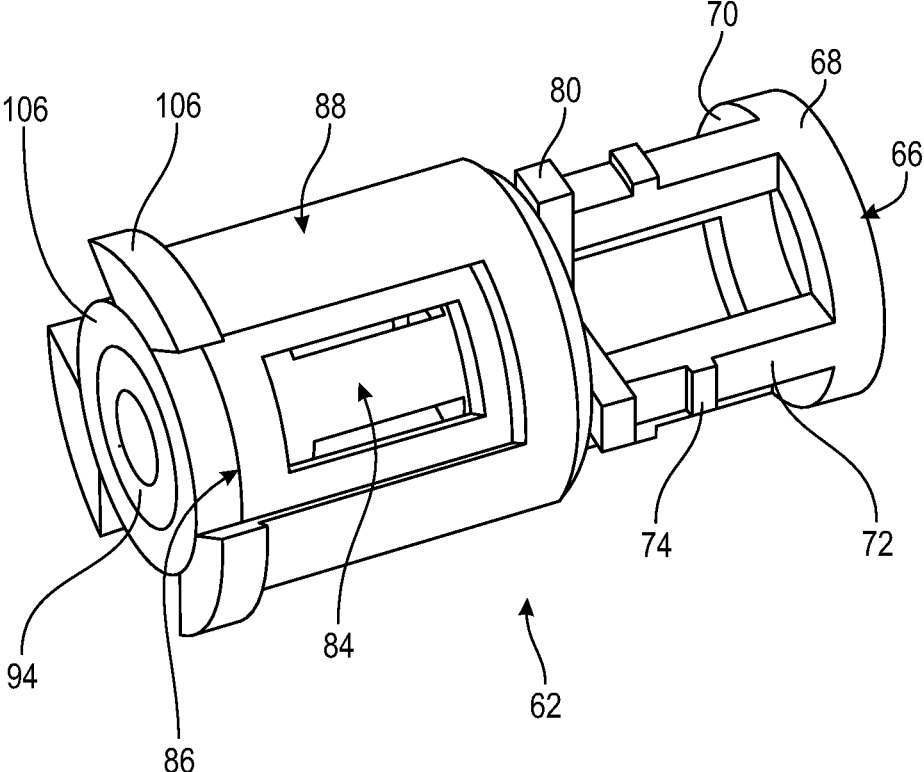
FIG. 7 is a perspective view of a telescoping actuator assembly of the syringe of FIG. 1 in its fully collapsed configuration; another embodiment of a dual chamber syringe, where each chamber contains fluid.

Referring to FIGS. 5-7, the collet bushing 66 of the telescoping actuator assembly 62 has plural bushing fingers 72, which respectively define a circumferential flange 74 that is in friction-tight engagement with the cylindrical wall that defines the proximal cavity 40 within the medication stopper 36. Proximal axial tips 76 of the respective collet bushing fingers 72 are coupled to and in abutting contact with a cruciform-shaped platform 80 of the actuator shaft 78. The actuator shaft defines a proximal, bulbous profile end 82. Nested distal 84, intermediate 86 and proximal 88 hollow tubes of the telescoping actuator assembly 62 couple the saline stopper 48 to the actuator 64, as follows.

As viewed sequentially from the distal end 28 toward the proximal end 24 of the syringe barrel 22, The bulbous-profiled end 82 of the actuator shaft 78 is retained within and is in frictional contact with an inner wall surface 90 of the distal telescoping tube 84. The distal telescoping tube 84 defines a through aperture 92 for passage of fluid there through, and a circumferential flange 94. The circumferential flange 94 of the telescoping distal tube 84 is retained within and is in frictional contact with an inner wall surface 96 of the proximal tube 88. The proximal telescoping tube 88 defines a through aperture 98 for passage of fluid there through, and a circumferential flange 100. The circumferential flange 100 of the telescoping intermediate tube 86 is retained within and is in frictional contact with an inner wall surface 102 of the proximal tube 88. The proximal telescoping tube 88 defines a through aperture 104 for passage of fluid there through, and a circumferential flange 106. The circumferential flange 106 of the telescoping proximal tube 88 is retained within the circumferential groove 53 formed within the distal cavity 52 of the saline stopper 48. When the telescoping actuator assembly 62 fully extended (FIGS. 5 and 6), its axial length is sufficient to enable extension of the actuator 64 away from contact with the corresponding seating surface 47 of the medication stopper 36, to enable selective fluid communication between the secondary chamber 108 and the syringe outlet 32. In order to prevent collapse of the telescoping tubes 82, 84, 86 during advancement of the syringe plunger 56, during drug delivery or aspiration of air from the primary/drug chamber 110, frictional force generated within the telescoping actuator assembly 62, between any contacting pair of the bulbous-profiled end 82, the circumferential flanges 94, 100 and its corresponding inner wall surface 90, 96 102 is greater than the combined frictional force generated between the medication stopper 36 and the barrel inner wall 22 and axial force necessary to advance the collet bushing 66 distal the seating surface 47 of the medication stopper 36. When external axial force exerted on the advancing plunger 56 exceeds the aforementioned combined frictional force generated within the telescoping actuator assembly 62, it collapses that assembly.

Figure 13:
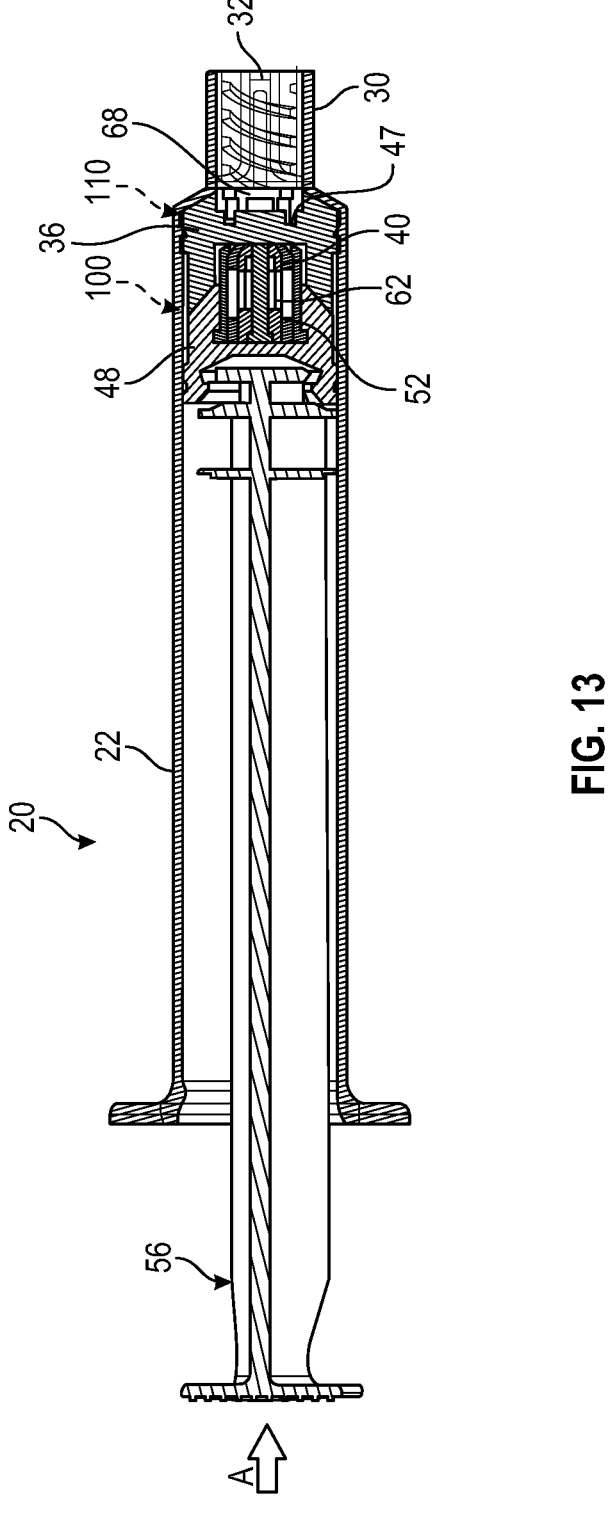

The telescoping distal tube 84, intermediate tube 86 and the actuator shaft 78 collapse within the proximal telescoping tube 88, when the plunger is fully advanced within the syringe barrel 22, as shown in FIG. 13. The collapsed, nested tubes 82, 84, 88 actuator shaft 78 and the cruciform platform 80 have an axial length less than the combined axial length of the distal cavity of the saline stopper 48 and the proximal cavity 40 of the medication stopper 36, so that the secondary chamber 108 is fully collapsed.

While the syringe 20 embodiment comprises three nested telescoping tubes 84, 86 and 88 mated with the actuator shaft 78 of the actuator 64, other syringe embodiments have a single tube mated with an actuator shaft. Yet other syringe embodiments have two nested tubes mated with an actuator shaft. Additional syringe embodiments comprise more than three nested telescoping tubes.

Figure 10:
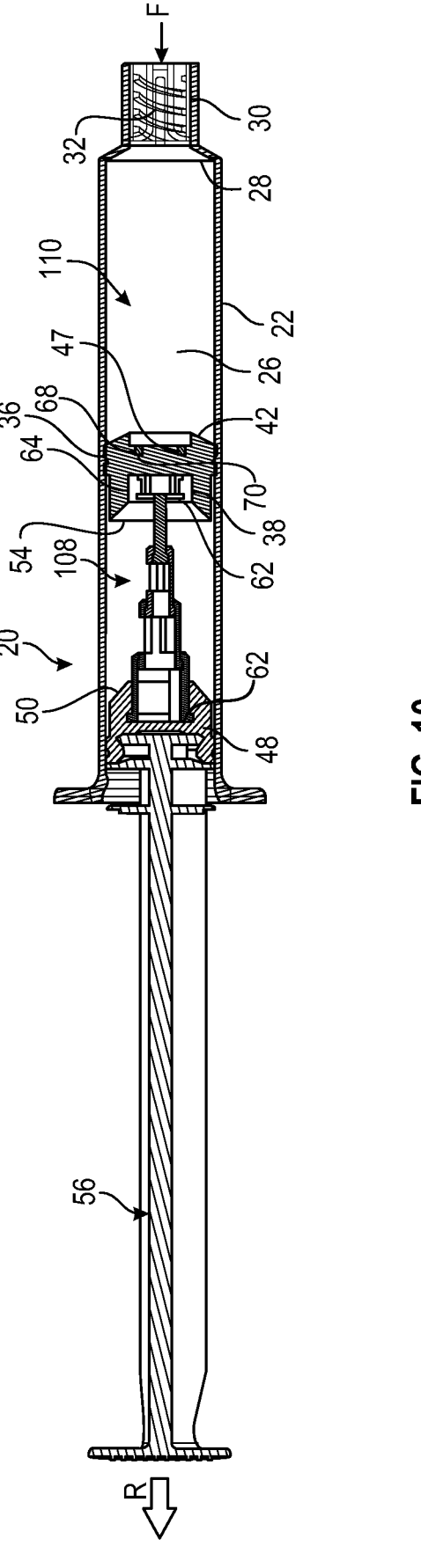
FIGS. 10-13 are illustrative, sequential steps, respectively showing medication aspiration in the medication or primary chamber of the syringe of FIG. 8, followed by dispensing/infusing of medication, followed by actuating or opening the fluid path of the prefilled or secondary chamber and lastly delivery of flushing liquid from the secondary chamber.

As shown in FIGS. 1 and 10, the syringe 20 is a dual chamber syringe with tandem, axially aligned and oriented, variable volume, secondary 108 and primary 110 chambers. The primary chamber 110 is defined circumferentially within the barrel inner wall 26 and axially by the distal face 42 of the medication stopper 36 and the distal axial end 28 of the barrel 22. The secondary chamber 108 is defined circumferentially within the barrel inner wall 26 and axially by the distal face 50 of the saline stopper 48 and the proximal distal axial end 38 of the medication stopper 36. The telescoping actuator assembly 62 functions as a manually actuated, selective isolation valve that facilitates discharge of fluid from the secondary chamber 108. Plunger clip 112, which is also referred to as a plunger collar prevents inadvertent advancement of the plunger 56, and is removed by a healthcare practitioner (see, e.g., FIGS. 1, 8, 14 and 15) prior to use of the syringe 20. In one or more embodiments, the variable volume, primary chamber 110 is pre-filled with or filled at the patient treatment site with a desired medicine. In one or more embodiments, the variable volume, secondary chamber 108 is pre-filled with a desired amount of a saline or other flush or diluent fluid. In one or more embodiments, the primary chamber 108 is pre-filled with a liquid or powdered/lyophilized drug during or after the assembly of the syringe 20 and the secondary chamber 110 is pre-filled with saline, other flushing fluid or another drug diluent. using sterile filling methods. In some embodiments, the barrel 22 of the syringe 20 includes measuring indicia (not shown) to indicate the amount of fluid contained within.

FIGS. 1, 2, 8-14 depict functional operation of an embodiment of the syringe 20, where its secondary chamber 108 is pre-filled with a flushing fluid, such as saline and packaged for shipment to and use by a healthcare facility. FIG. 1 depicts the syringe 20 in its shipped state, after removal of external packaging, but prior to removal of the male Luer cap 34. A plunger clip/plunger collar 112 circumscribes the plunger 56 between the latter's proximal end 60 and the proximal end 24 of the syringe barrel 22, to inhibit inadvertent advancement of the plunger. As shipped, the distal end 42 of the medication stopper 36 is in abutting contact with the distal end 28 of the syringe barrel 22, so that the primary chamber 108 is fully collapsed and empty. The telescoping actuator assembly 62 isolates the secondary chamber from communication with the outlet 32 (FIG. 2), preventing leakage of the saline fluid out of the syringe. The plunger clip/plunger collar 112 and the male Luer cap 34 are removed from the syringe 20 prior to its use.

Figure 8:
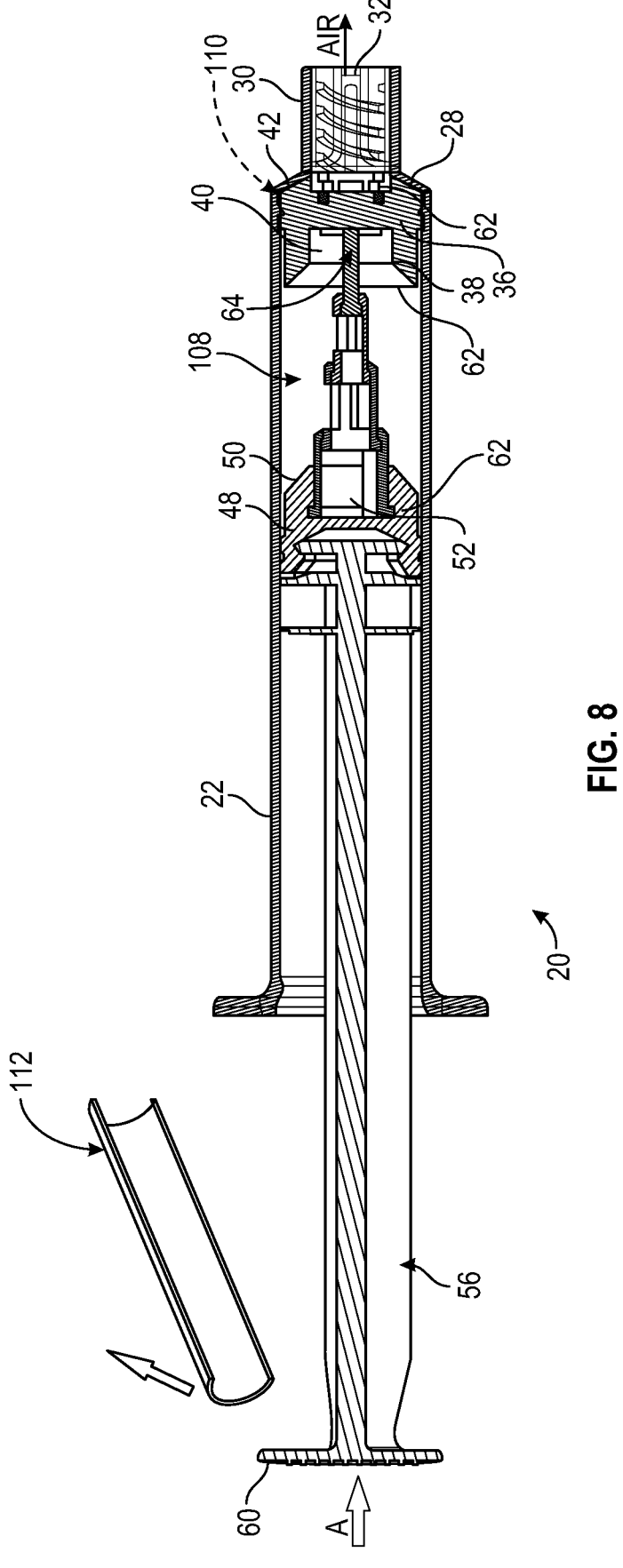
FIG. 8 shows removal of trapped air from the pre-filled chamber of the syringe of FIG. 1.
Figure 9:
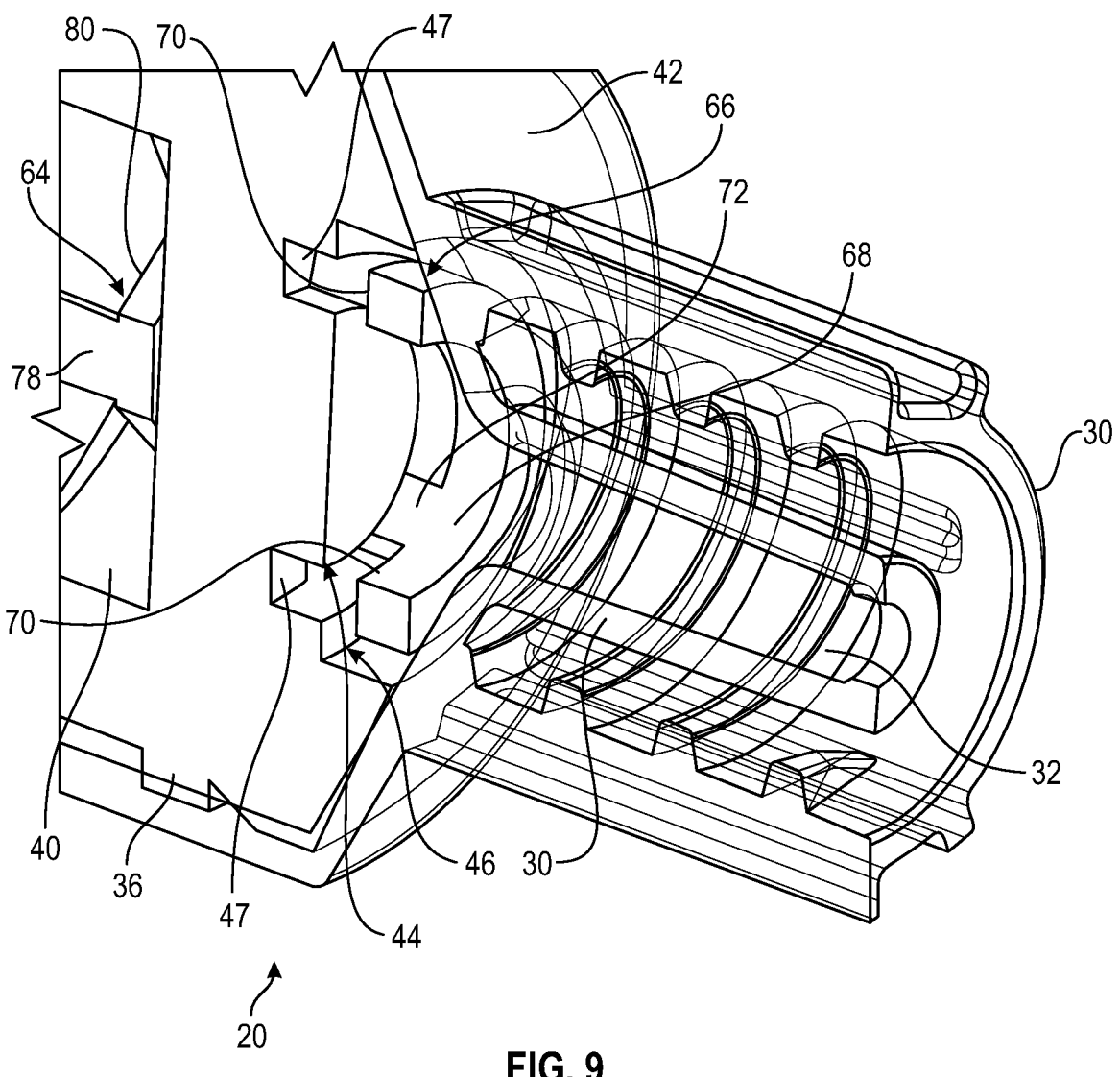
FIG. 9 is an enlarged, cross-sectional view of the distal portion of the syringe of FIG. 8.

FIGS. 8 and 9 depict removal of air trapped within the pre-filled secondary chamber 108 of the pre-packaged syringe 20, by advancing the plunger 56 (the arrow A) sufficiently to separate the proximal face 70 of the bushing rim 68 of the actuator 64 from contact with the seating surface 47 of the medication stopper 36. In this partially advanced state of the plunger 56, separation of the actuator 64 from the seating surface 47 allows fluid communication among the secondary chamber 108, the proximal cavity 40, the fluid through-passage 44 and the outlet 32 of the Luer tip 30, in turn allowing trapped air to escape from the secondary chamber 108.

FIG. 10 depicts aspiration of medication into the primary chamber 110 by withdrawing or retracting the plunger 56 (arrow R). Retraction of plunger 56 tensions the telescoping actuator assembly 62, which seats the proximal face 70 of the collet bushing rim 68 against the corresponding seating surface 47 of the medication stopper 36. Retraction of the plunger 56 also creates a negative pressure differential in the primary chamber 110 relative to ambient pressure in the outlet 32; this assists maintaining contact between the proximal face 70 and the seating surface 47 (i.e., re-isolates the secondary chamber 108 by closing the valve) while simultaneously aspirating medication into the primary chamber from a medication vial (not shown).

Figure 11:
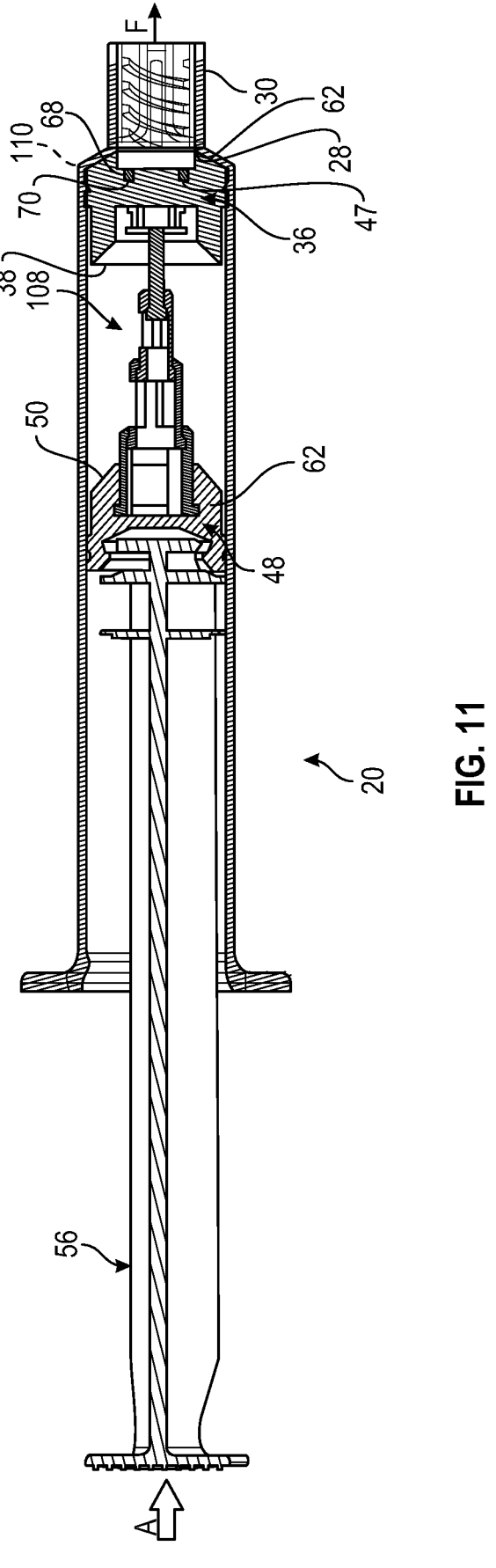

FIG. 11 depicts medication delivery to a (not shown) VAD of a patient. The medication is infused from the primary chamber 110 into a previously flushed VAD, by advancing the plunger 56 (arrow A), thereby emptying the primary chamber. Advancing pressure applied to the plunger 56 is sufficient to advance the medication stopper 36 to contact with the distal end 28 of the syringe barrel 22, but not so hard as to advance the actuator 64 out of contact with the seating surface 47 of the medication stopper.

Figure 12:
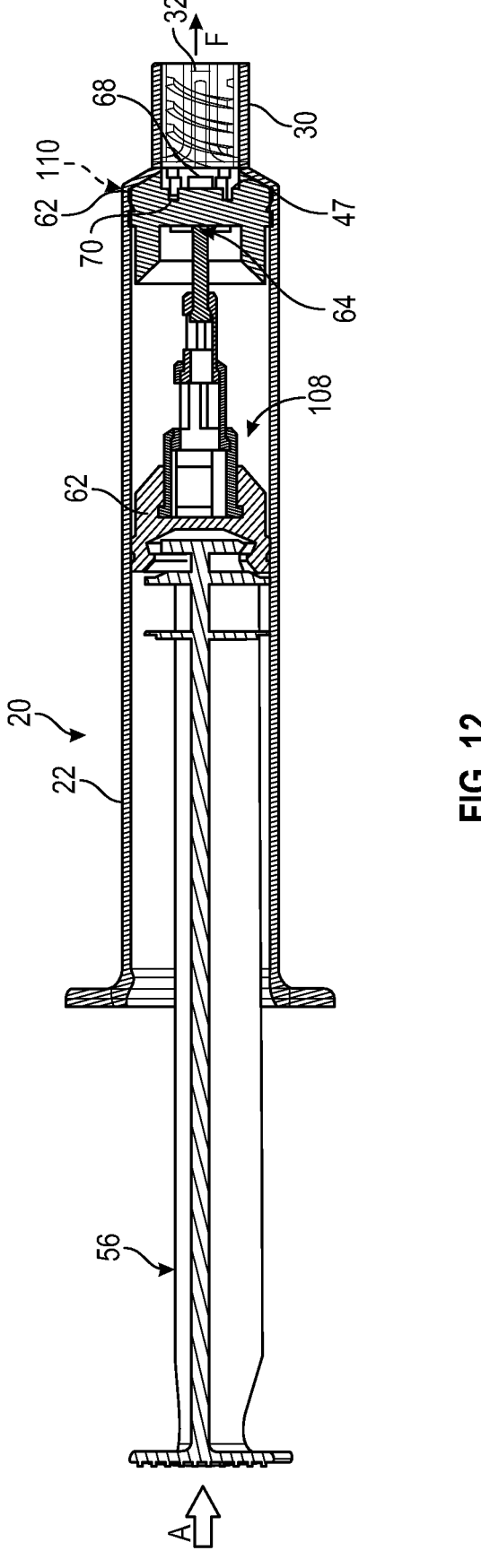

In FIGS. 12 and 13, The VAD is flushed with flushing solution (e.g., saline or heparin) pre-packaged in the secondary chamber 108, by advancing the plunger 56 with sufficient pressure to advance the actuator 64 out of contact with the seating surface 47 of the medication stopper (FIG. 12). This opens the valve and delivers the flushing solution out of the outlet 32 of the syringe 20 (FIG. 13) until the secondary chamber 108 is collapsed and empty. Upon completion of the flushing procedure, the syringe 20 is then withdrawn from the VAD.

Figure 14:
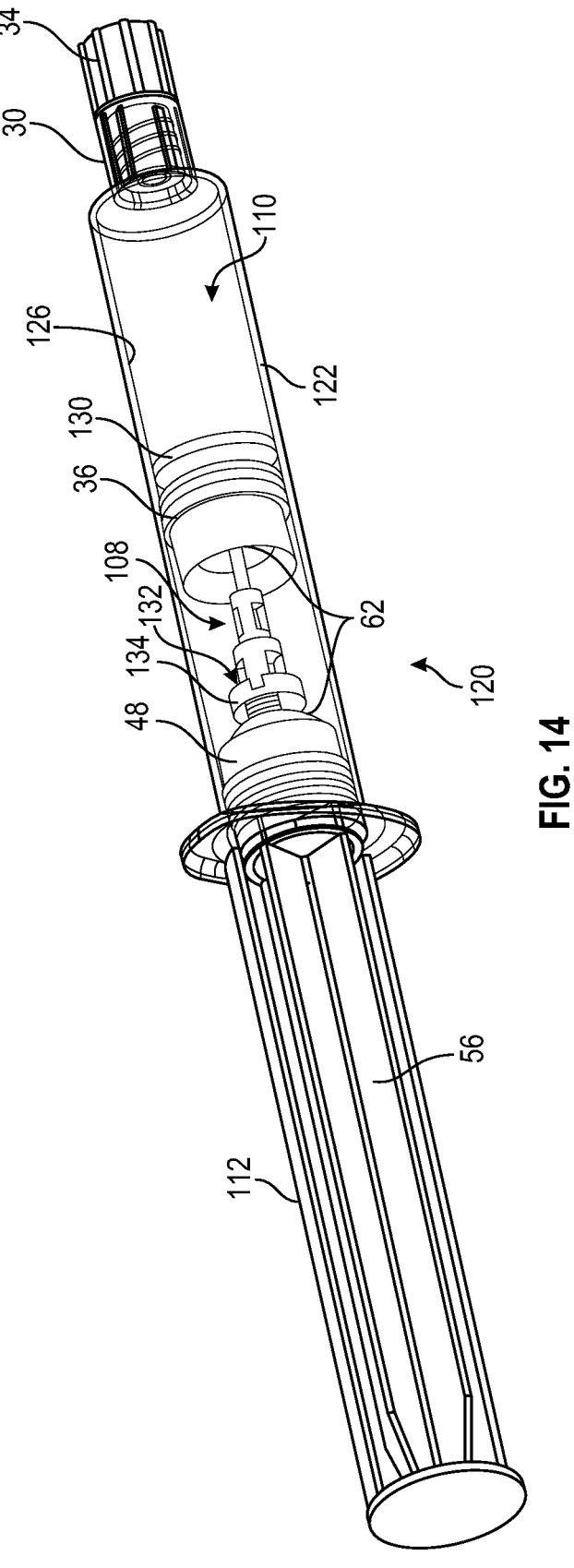
FIG. 14 is perspective view of an embodiment of a dual chamber, drug mixing syringe, where the secondary chamber is pre-filled with diluent and the primary, drug delivery chamber, is pre-filled with powdered/lyophilized drug.
Figure 15:
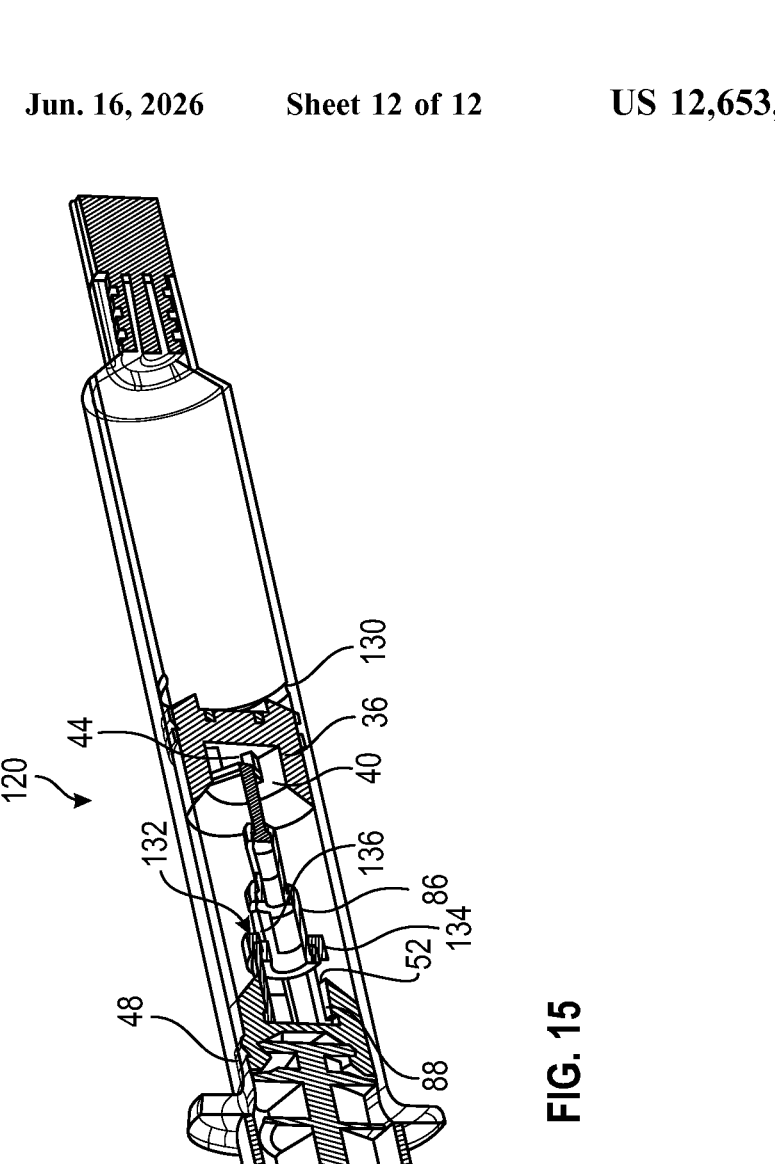
FIG. 15 is a cross-sectional view of the syringe of FIG. 14.

Another aspect of the present disclosure is shown in FIGS. 14 and 15, wherein the dual chamber syringe 120 (of similar construction as the syringe 20) facilitates mixing of pre-filled powdered/lyophilized drug in the primary chamber 110 with pre-filled diluent (e.g., saline) in the secondary chamber 108. A radially inwardly projecting barrel ring 130 formed on the inner wall of 126 of the syringe barrel 122 inhibits advancement of the medication stopper 36 distally beyond the ring. Advancement pressure on the plunger 56 that is necessary to overcome advancement resistance of the barrel ring 130 is higher than the advancement pressure needed to advance the telescoping actuator assembly 62 beyond engagement with the medication stopper 36 and allow saline to flow from the secondary chamber 108 into the primary/mixing chamber 110. After removal of the plunger clip/collar 112 from the plunger 56 and subsequent advancement of the plunger toward the barrel ring 130, the telescoping actuator assembly 62 opens the medication stopper fluid passage 44, allowing the saline or other diluent to mix with the drug. After shaking or otherwise agitating the drug/diluent mix, the male Luer cap 34 is removed from the syringe 120 and the syringe plunger 56 is advanced sufficiently to remove trapped air from the primary chamber 108. The now mixed medication 120 is delivered after attaching the Luer connector 30 to a VAD. A path seal 132 circumscribes the telescoping actuator assembly to prevent backflow or reflux of the diluent/drug mixture from the primary chamber 110 to the secondary chamber 110 via the medication stopper fluid passage 44. An outer circumference 134 of the path seal 132 abuts against or within the proximal cavity 40 in the medicine stopper 36, while an inner circumference 136 thereof abuts against respective outer circumferential surfaces of the intermediate telescoping tube 86 and the proximal telescoping tube 88.

While separate and alternative syringe embodiments 20 and 120 are shown and described herein, either embodiment is capable of being used for: (a) sequential administration of different pre-filled drugs in both of their respective primary 110 and secondary 108 chambers, or (b) aspiration/administration of a drug in their respective primary chambers followed by administration of another drug from their respective secondary chambers, or (c) aspiration/administration of a drug in their respective primary chambers followed by flushing a VAD with pre-filled flushing fluid in their respective secondary chambers, or (d) administration of a pre-filled drug in their respective primary chambers followed by flushing a VAD with pre-filled flushing fluid in their respective secondary chambers, or (e) mixing of a pre-filled powdered/lyophilized drug in their respective primary chambers followed by flushing a VAD with pre-filled flushing fluid in their respective secondary chambers.

The single syringe 20 facilitates sequential delivery of a pre-filled or on-site aspirated drug within its primary chamber 110 to a patient's VAD, followed by immediate flushing of the VAD with pre-filled saline or other flushing fluid contained within its primary chamber, with a single, continuous stroke of the syringe plunger 56. The syringe 20 does not require manipulation of multiple plungers, non-linear or compound plunger motions, or external valves to deliver sequentially medication and flushing fluid. A single syringe 20 performs both the medication delivery and flushing procedures typically performed with separate syringes. As previously noted, simplifying drug delivery and flushing by use of a single syringe 20 reduces costs associated with purchasing of multiple syringes. In some embodiments, the single syringe 20 reduces risk of patient drug delivery errors because the drug and/or flushing solution are already prefilled in the syringe. In some embodiments, the single syringe 20 reduces risk that a patient's VAD is not flushed after drug administration due to distraction of the healthcare professional because the flushing solution is already prefilled in the secondary chamber 108. Simply, the professional is more likely to complete advancement of the single plunger 56 stroke with the sequential delivery syringe 20 after she or he completes the drug administration, rather than needing to replace the drug syringe with a new and separate flushing syringe. Sequential drug administration and VAD flushing with a single syringe 20 also reduces infection risk attributable to multiple piercings of the VAD's septum by separate syringes. Lastly, the syringe 20, with its telescoping actuator assembly 64 does not require puncturing of the medication stopper 36 in order to discharge flushing solution from its secondary chamber 108; this reduces potential infiltration of damaged stopper particulate matter into the VAD or the patient.

The syringe 120 facilitates mixing of pre-filled powdered/ lyophilized drug in the primary chamber 110 with pre-filled diluent (e.g., saline) in the secondary chamber and subsequent, delivery of the mixed drug with a single, continuous stroke of the syringe plunger 56. The syringe 120 does not require manipulation of multiple plungers, non-linear or compound plunger motions, or external valves to mix and administer medication sequentially. In some embodiments, the single syringe 120 reduces risk of patient drug delivery errors because the drug and diluent are already pre-filled in the syringe. The syringe 120, with its telescoping actuator assembly 64 does not require puncturing of the medication stopper 36 in order to discharge diluent from its secondary chamber 108 into the primary chamber 110; this reduces potential infiltration of damaged stopper particulate matter into the VAD or the patient.

The syringe embodiments disclosed herein are constructed from medical grade materials known to one skilled in the art. In some embodiments, described barrels, plungers and shafts are fabricated with polypropylene polymers. Seals are fabricated with fiber-filled polytetrafluoroethylene (PTFE) polymers. Stoppers are fabricated with polyisoprene polymers.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are to be interpreted broadly; they encompass direct and indirect mountings, connections, supports, and couplings. Further, "connected" and "coupled" are not restricted to physical, mechanical, or electrical connections or couplings.

Although the disclosure herein provided a description with reference to embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents. The appended claims are not limited to the exemplary embodiment details of construction and the arrangement of components set forth in the description or illustrated in the drawings.

What is claimed is:

1. A sequential drug delivery syringe, comprising:
a hollow syringe barrel defining an inner wall, a proximal barrel end and a distal barrel end, the distal end of the barrel including a connector defining an outlet lumen therethrough, the outlet lumen in fluid communication with an interior of the barrel, the barrel interior defined by the proximal barrel end, the distal end, and the inner side wall;
a plunger disposed with the barrel interior, having a proximal end extending outside of the proximal end of the barrel and a distal end;
a secondary stopper disposed within the barrel interior, having: a proximal axial end coupled to the distal end of the plunger, and a distal axial end defining a distal cavity therein;
a primary stopper disposed within the barrel interior between the secondary stopper and the distal end of the barrel, having: a proximal axial end defining a proximal cavity, a distal axial end defining a distal cavity with a seating surface a defining a through-passage in fluid communication with both of the proximal and distal cavities thereof;
a telescoping actuator assembly oriented with the respective cavities of the primary and secondary stoppers, having:
a reciprocating actuator oriented within the through-passage of the primary stopper, the actuator projecting into the proximal and distal cavities of said primary stopper and having: an outer circumferential surface in sliding, friction engagement with the through-passage, and a radially projecting, proximal axial face that is oriented within the corresponding distal cavity of the primary stopper, in opposed orientation with the seating surface, and
a tube having: an outer circumferential surface coupled to and within the distal cavity of the secondary stopper, and an inner wall circumscribing and in sliding, friction engagement with the outer circumferential surface of the actuator;
a primary fluid chamber within the barrel interior, defined between a distal end surface of the primary stopper and outlet lumen at the distal end of the barrel, a volume of the primary fluid chamber being selectively variable by translation of the plunger; and
a secondary fluid chamber, within the barrel interior, defined between a distal end surface of the secondary stopper and the through-passage of the primary stopper, a volume of the secondary fluid chamber being selectively variable by translation of the plunger when the proximal axial face of the actuator is spaced away from the seating surface of the primary stopper;
wherein the secondary fluid chamber is in fluid communication with the primary fluid chamber and the outlet lumen of the syringe when the proximal axial face of the actuator is spaced away from the seating surface of the primary stopper, and the secondary fluid chamber is isolated from the primary fluid chamber when the proximal axial face of the actuator is in abutting contact with the seating surface of the primary stopper;

wherein withdrawal of the plunger tensions the telescoping actuator assembly, which reciprocates the proximal axial face of the actuator into abutting contact with the seating surface of the primary stopper, and withdraws said primary stopper; and wherein advancement of the plunger alone advances the primary stopper, reciprocates the proximal axial face of the actuator away from abutting contact with the seating surface of the primary stopper, advances the secondary stopper, and collapses the telescoping actuator assembly within the respective distal cavity of the secondary stopper and the proximal cavity of the primary stopper.

2. The syringe of claim 1, the actuator assembly further comprising plural nested tubes in sliding, friction engagement with each other, each nested tube respectively having an outer circumferential surface and an inner wall; an outer circumferential surface of a most proximally oriented one of which being coupled to and within the distal cavity of the secondary stopper, with its inner wall in sliding, friction engagement with the outer circumferential surface of an adjoining tube captured therein; and the inner wall of a most distally oriented one of which circumscribing and in sliding, friction engagement with the outer circumferential surface of the actuator.

3. The syringe of claim 2, the actuator further comprising: a collet bushing having an annular bushing rim, the annular bushing rim having a radially projecting, proximal axial face thereof in opposed orientation with the seating surface of the primary stopper, a plurality of collet bushing fingers projecting away from the radially projecting, proximal axial face of the annular bushing rim, in friction contact with the seating surface defining the through-passage, a distal tip of each bushing finger projecting into the proximal cavity of the primary stopper.

4. The syringe of claim 3, the actuator further comprising: the distal tips of the collet bushing fingers coupled to a platform of a distal end of an actuator shaft, an outer surface of a proximal end of the actuator shaft in sliding friction engagement with the inner wall of the distal-most oriented tube, the seating surface of the primary stopper captured between the collet bushing and the platform.

5. The syringe of claim 4, at least one of the collet bushing fingers defining an outwardly radially projecting, circumferential flange that is in friction contact with the seating surface defining the through-passage.

6. The syringe of claim 5, wherein the plurality of collet bushing fingers comprising four uniformly circumferentially spaced collet fingers rigidly coupled to the corresponding cruciform-shaped platform of the actuator shaft, the proximal outer surface of the actuator shaft defining a bulbous surface profile for frictional engagement with the corresponding inner wall surface of the distal-most oriented tube.

7. The syringe of claim 6, wherein the plural nested tubes comprise three nested tubes, the proximal-most oriented of which defines an outer circumferential flange at a distal end thereof that is in mating engagement with a corresponding circumferential groove defined within the distal cavity of the secondary stopper, and the inner wall surface of the distal-most oriented of which is in friction engagement with the bulbous surface of the actuator shaft.

8. The syringe of claim 1, the actuator further comprising: a collet bushing having an annular bushing rim, a radially projecting, proximal axial face thereof in opposed orientation with the seating surface of the primary stopper, a plurality of collet bushing fingers projecting away from the proximal axial face of the annular bushing rim, in friction contact with the seating surface defining the through-passage, a distal tip of each bushing finger projecting into the proximal cavity of the primary stopper.

9. The syringe of claim 8, the actuator further comprising: the distal tips of the collet bushing fingers coupled to a platform of a distal end of an actuator shaft, an outer surface of a proximal end of the actuator shaft in sliding friction engagement with the inner wall of the tube, the seating surface of the primary stopper captured between the collet bushing and the platform.

10. The syringe of claim 9, at least one of the collet bushing fingers defining an outwardly radially projecting, circumferential flange that is in friction contact with the seating surface defining the through-passage.

11. The syringe of claim 10, wherein the plurality of collet bushing fingers comprising four uniformly circumferentially spaced collet fingers rigidly coupled to the corresponding cruciform-shaped platform of the actuator shaft, the proximal outer surface of the actuator shaft defining a bulbous surface profile for frictional engagement with the corresponding inner wall surface of the tube.

12. The syringe of claim 1, further comprising: an inwardly radially projecting barrel ring formed on the inner wall of the barrel, and a path seal having an inner circumferential surface circumscribing the outer surface of the tube of the actuator assembly and an outer circumferential surface in fluid sealing contact with the proximal cavity of the primary stopper, the path seal inhibiting backflow of fluid from the primary chamber to the secondary chamber.

13. A sterile, pre-packaged syringe of claim 12, further comprising a dry or powdered drug in the primary chamber, and a drug diluent in the secondary chamber thereof.

14. The syringe of claim 1, the distal end of the primary stopper and the distal end of the syringe barrel having corresponded, mating profiles that contact each other when the primary stopper is fully inserted into to the interior of the syringe barrel, so that volume of the primary fluid chamber is minimized.

15. The syringe of claim 1, the proximal end of the primary stopper and the distal end of the secondary stopper having corresponded, mating profiles that contact each other when the secondary stopper is fully inserted into to the interior of the syringe barrel, so that volume of the secondary fluid chamber is minimized.

16. A sterile, pre-packaged syringe of claim 1, further comprising flushing fluid in the secondary chamber thereof.

17. The syringe of claim 1, wherein: advancement of the plunger at a first axial pressure advances the primary stopper, and advancement of the plunger at a second axial pressure greater than the first pressure reciprocates the proximal axial face of the actuator away from abutting contact with the seating surface of the primary stopper, which establishes fluid communication among the secondary and primary fluid chambers and the outlet lumen and advances the secondary stopper.

18. A sequential drug delivery syringe, comprising:
   a hollow syringe barrel defining an inner wall, a proximal barrel end and a distal barrel end, the distal end of the barrel including a connector defining an outlet lumen therethrough, the outlet lumen in fluid communication with an interior of the barrel, the barrel interior defined by the proximal barrel end, the distal end, and the inner side wall;
   a plunger disposed with the barrel interior, having a proximal end extending outside of the proximal end of the barrel and a distal end;

a secondary stopper disposed within the barrel interior, having: a proximal axial end coupled to the distal end of the plunger, and a distal axial end defining a distal cavity therein;

a primary stopper disposed within the barrel interior between the secondary stopper and the distal end of the barrel, having: a proximal axial end defining a proximal cavity, a distal axial end defining a distal cavity with a seating surface, and a defining a through-passage in fluid communication with both of the proximal and distal cavities thereof;

a telescoping actuator assembly oriented with the respective cavities of the primary and secondary stoppers, having:

plural nested tubes in sliding, friction engagement with each other, each nested tube respectively having an outer circumferential surface and an inner wall, an outer circumferential surface of a most proximally oriented one of which being coupled to and within the distal cavity of the secondary stopper, with its inner wall in sliding, friction engagement with the outer circumferential surface of an adjoining tube captured therein, and a reciprocating actuator oriented within the through-passage of the primary stopper, the actuator including a collet bushing having an annular bushing rim, a radially projecting, proximal axial face thereof in opposed orientation with a mating, annular-shaped seating surface of the primary stopper, a plurality of collet bushing fingers projecting away from the proximal axial face of the annular bushing rim, in friction contact with the surface defining the through-passage, a distal tip of each bushing finger projecting into the proximal cavity of the primary stopper, the distal tips of the collet bushing fingers coupled to a platform oriented on a distal end of an actuator shaft, an outer surface of a proximal end of the actuator shaft in sliding friction engagement with the inner wall of the distalmost oriented tube, the seating surface of the primary stopper captured between the collet bushing and the platform;

a primary fluid chamber within the barrel interior, defined between a distal end surface of the primary stopper and outlet lumen at the distal end of the barrel, volume of the primary fluid chamber being selectively variable by translation of the plunger; and a secondary fluid chamber, within the barrel interior, defined between a distal end surface of the secondary stopper and the through-passage of the primary stopper, volume of the secondary fluid chamber being selectively variable by translation of the plunger when the proximal axial face of the annular bushing rim is spaced away from the seating surface of the primary stopper;

wherein the secondary fluid chamber is in fluid communication with the primary fluid chamber and the outlet lumen of the syringe when the proximal axial face of the annular bushing rim is spaced away from the seating surface of the primary stopper, and the secondary fluid chamber is isolated from the primary fluid chamber when the proximal axial face of the annular bushing rim is in abutting contact with the seating surface of the primary stopper;

wherein withdrawal of the plunger tensions the telescoping actuator assembly, reciprocates the proximal axial face of the of the annular bushing rim into abutting contact with the seating surface of the primary stopper, and withdraws said primary stopper; and wherein advancement of the plunger alone at a first axial pressure advances the primary stopper, advancement of the plunger at a axial second pressure greater than the first axial pressure reciprocates the proximal axial face of the annular bushing rim away from abutting contact with the seating surface of the primary stopper, which establishes fluid communication among the secondary and primary fluid chambers and the outlet lumen and advances the secondary stopper; and advancement of the plunger at a third axial pressure greater than the second axial pressure collapses the telescoping actuator assembly within the respective distal cavity of the secondary stopper and the proximal cavity of the primary stopper.

19. A method for making the syringe of claim 18 comprising:

inserting the collet bushing fingers into the through-passage of the primary stopper so that they project into the proximal cavity thereof;

rigidly coupling the platform of the actuator assembly to the tips of the collet bushing fingers, capturing the primary stopper between the annular rim of the collet bushing and the cruciform platform;

coupling the proximal-most oriented tube of the actuator assembly within the distal cavity of the secondary stopper before or after coupling the plunger to the secondary stopper; and inserting the now coupled primary stopper, actuator assembly, secondary stopper and the plunger into the interior of the syringe barrel.

20. The syringe of claim 18, further comprising: an inwardly radially projecting barrel ring formed on the inner wall of the barrel, and a path seal circumscribing the telescoping actuator assembly actuator assembly and an outer circumferential surface of the path seal in fluid sealing contact with the proximal cavity of the primary stopper, the path seal inhibiting backflow of fluid from the primary chamber to the secondary chamber.

* * * * *